United States Patent [19]
Losee et al.

[11] Patent Number: 5,785,957
[45] Date of Patent: Jul. 28, 1998

[54] INCLUSION OF TOOTH WHITENING OXIDATION CHEMISTRIES INTO A TOOTHPASTE COMPOSITION

[76] Inventors: Paul Losee, 2783 N. Highway 89, Layton, Utah 84041; F. Richard Austin, 2045 E. 2200 North, Layton, Utah 84090; Blaine D. Austin, 1811 N. Forest Ridge, Layton, Utah 84040

[21] Appl. No.: 783,385

[22] Filed: Jan. 13, 1997

Related U.S. Application Data

[63] Continuation-in-part of Ser. No. 571,133, Dec. 12, 1995.

[51] Int. Cl.$^6$ .............. A61K 7/16; A61K 7/20; A61K 33/40; A61K 47/26
[52] U.S. Cl. .............. 424/53; 424/49; 424/613; 514/777
[58] Field of Search .............. 424/49–58, 613; 514/777

[56] References Cited

U.S. PATENT DOCUMENTS

| | | | |
|---|---|---|---|
| 3,574,824 | 4/1971 | Echeandia et al. | 424/50 |
| 4,587,119 | 5/1986 | Bucke et al. | 424/49 |
| 4,837,068 | 6/1989 | Rudy et al. | 404/53 |
| 4,897,258 | 1/1990 | Rudy et al. | 424/53 |
| 4,971,782 | 11/1990 | Rudy et al. | 424/53 |
| 4,988,500 | 1/1991 | Hunter et al. | 424/53 |
| 5,171,564 | 12/1992 | Nathoo | 424/53 |
| 5,256,402 | 10/1993 | Prencipe et al. | 424/53 |
| 5,264,205 | 11/1993 | Kelly | 424/53 |
| 5,597,554 | 1/1997 | Wagner | 424/53 |
| 5,631,000 | 5/1997 | Pellico et al. | 424/53 |

*Primary Examiner*—Shep K. Rose
*Attorney, Agent, or Firm*—James L. Sonntag

[57] ABSTRACT

A tooth-paste composition for whitening teeth and method for manufacture, the composition comprising a water-free, non-hygroscopic base and carbamide peroxide.

5 Claims, 1 Drawing Sheet

Figure
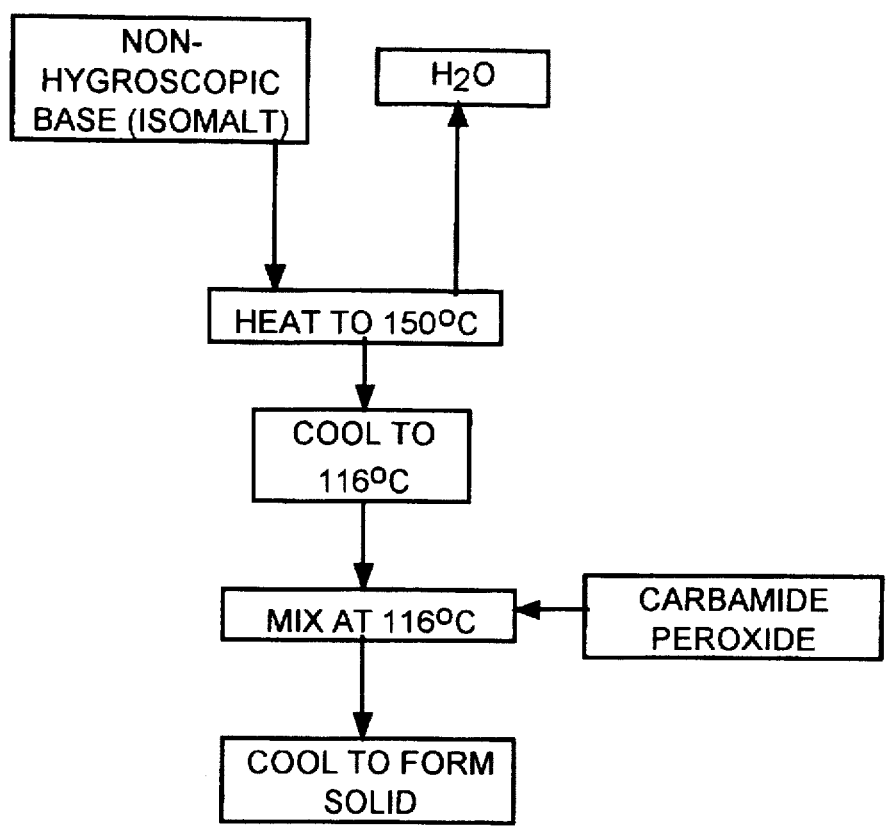

INCLUSION OF TOOTH WHITENING OXIDATION CHEMISTRIES INTO A TOOTHPASTE COMPOSITION

RELATED APPLICATIONS

This application is a Continuation-in-part of application Ser. No. 08/571,133, filed 12 Dec. 1995 which is pending.

STATEMENT REGARDING FEDERALLY SPONSORED RESEARCH OR DEVELOPMENT (Not applicable)

FIELD OF THE INVENTION

This invention relates to a preparation for introduction of whitening chemicals to the surface of teeth and method of use and manufacture. More particularly, the present invention relates to such preparations in a solid or tablet form, which is less costly and easier to use for the consumer than existing products available.

BACKGROUND OF THE INVENTION

The anatomy of a tooth is well known with an inner dentin layer and an outer hard surface enamel layer. Enamel is an opaque white or off-white color. It is the enamel that can become stained and/or discolored. The porous nature of the enamel layer allows stain and discoloring substances to enter the enamel surface and thereby discolor the tooth.

Many substances and food items, such as juices, tea, coffee and tobacco, can "stain" or reduce the "whiteness" of teeth. These substances are consumed on a daily basis and gradually over several months or years can impart a noticeable discoloration of the enamel surfaces of the teeth.

Presently the dental profession uses methods to whiten teeth that are based on the presentation of either hydrogen peroxide or carbamide peroxide in a gel preparation to the enamel surfaces of the teeth. These compounds come in varying strengths from 10 wt. % to 35 wt. %. The gels are delivered either by the dentist in the dental office, accompanied by light and/or heat, or by using home-use kits via plastic trays fitted to the teeth.

The home-use kits, which use low concentration compounds, require the fabrication of a plastic tray filled with a whitening gel before placement over the teeth. For proper fitting, a dentist must usually fabricate the tray. The treatment time is high and the activities of the consumer are restricted while the tray is in place. Generally several treatments are required. The disadvantage of this system is the lengthy time required to whiten teeth and the high inconvenience accompanying its use.

Faster whitening is accomplished by the dentist in the office, where the higher concentration gels are used. However, the cost to the consumer is higher and there is additional risk of the higher concentrations causing some soft tissue irritation.

There is a demand in the marketplace for a less costly and more easily utilized whitening product which is without the constraints on time, the mess of the gels and lack of dental trays.

Candies, tablets, gums, and the like have been used as a vehicle for introducing various chemical agents to a tooth surface. A strict requirement, however, for these compositions is that they have a long shelf-life, at least on the order of several weeks. This requirement has limited the use of solids for tooth-whitening preparations because, in general, the active components for tooth-whitening are not stable under ambient conditions of humidity and temperature. In solid compositions, these components quickly become degraded to unsuitably low concentrations. In addition, the whitening compositions frequently degrade to reactions products with a bad taste. Thus, the compositions can become unpalatable even before the active component has degraded to insufficient levels.

An example of a tablet or gum or tooth treatment is disclosed in U.S. Pat. No. 4,302,441 issued to Muhlemann et al. on Nov. 24, 1981. This patent discloses a solid oral preparation comprising active urea hydrogen peroxide (carbamide peroxide) that is effective in countering acid fermentable carbohydrates in dental plaques. The solid oral composition in the form of a lozenge tablet or chewing gum comprises urea hydrogen peroxide and, in the absence of glycerol, and a sweetener selected from the group consisting of mannitol, sorbitol, xylitol and saccharin, and a carrier selected from the group consisting of soluble cellulose ethers and carbohydrate gums. These compositions may be effective in introducing carbamide peroxide to the surface of the teeth of the person to whom it is administered, but they suffer from having a short shelf life. In solid materials carbamide peroxide gradually reacts with ambient water such as from humidity in the air and with water in the composition to form urea and oxygen or hydrogen peroxide. This not only leads to a decrease in the effective amount of the carbamide peroxide, it also produces urea, which in small concentrations lends a sharp, unpleasant taste to the composition. Thus, even before the composition becomes ineffective from depletion of the carbamide peroxide it becomes unpalatable in only a few days and unacceptable as a consumer product.

OBJECTS OF THE INVENTION

It is, therefore, an object of the invention to provide a system for delivering whitening agents to tooth surfaces that overcomes the shortcomings of the prior-art gel systems.

It is also an object of the invention to provide a whitening composition with a long shelf-life that does not degrade quickly to become unpalatable or ineffective.

An object of the invention is also to provide a system that is less costly and can be used by the consumer in a manner that does not restrict activity and requires an undue amount of time.

It is further an object of the invention to provide a composition in a solid form that is commercially acceptable, that is, introduces a sufficient carbamide peroxide to the tooth surface to provide a whitening effect, but also to provide sufficient stability that the product over a storage period of several weeks will not decompose to form urea to give the product an unpleasant taste.

It further an object of the invention to provide a system that avoids the messy gels and liquids, and high peroxide concentrations.

Further objects will become evident in the description that follows.

BRIEF SUMMARY OF THE INVENTION

The invention involves a composition and method for manufacture for a solid orally administered formulation containing carbamide peroxide and a water-free base formulation that is non-hygroscopic. The formulation is stable, having a shelf life of several weeks.

The active ingredient in the present invention, carbamide peroxide, $CON_2H_4 \cdot H_2O_2$ is the addition compound of hydrogen peroxide and urea and is also known as urea peroxide, or urea hydrogen peroxide. The composition of the invention contains carbamide peroxide in a whitening effective amount, i.e., an amount to be efficacious to effect a whitening of teeth when taken orally (placed in the mouth) and chewed or dissolved to release the carbamide peroxide. A efficacious amount has been found to be greater than about 3 wt. %. If the amount of carbamide peroxide is too high, greater than about 12 wt. %, it may impart an unpleasant taste to the composition. Suitable amounts for a commercially suitable product have been found to be between about 3.5 wt. % and about 10 wt. %.

As mentioned above, carbamide peroxide when reacted with water decomposes into urea. In the compositions of the present invention, the carbamide peroxide is isolated from water while in the product, thus the solid product does not degrade and has a long shelf-life. As the product is placed in the mouth and slowly dissolved by the saliva, it reacts with the saliva to produce a bleaching effect on the tooth surface without producing an unpleasant taste. It has been found that any urea that is formed in this process of dissolution in the mouth is insufficient to impart a bad taste to the product.

It has been found that prior-art gum, tablet and gum compositions contain water, or often contain substances that attract water from the humidity in the air. In normal compositions this water is no problem, but if carbamide peroxide is present, that water is available to react with and degrade the carbamide peroxide to produce urea.

In the practice of the present invention, water is expelled from the composition of the invention and because of the inherent properties of the base of the composition of the invention, there is no reabsorption or attraction of water from the humidity in the air. Accordingly, the carbamide peroxide is protected or shielded from water and the decomposition reaction does not take place sufficiently to produce an unpleasant taste. Accordingly, it has been found that the compositions of the present invention can be stored for several weeks with no detectible deterioration in taste and with an insignificant loss of the active ingredient.

The base composition, for purposes of this disclosure, is the portion of the composition of the invention other than the carbamide peroxide component. The base of the present invention is essentially water-free and non- hygroscopic. By "water-free" is meant that it contains negligible water that is free to react with the carbamide peroxide. The composition may contain waters of hydration, but they must be bound sufficiently to the base composition or present in such a small amount to provide negligible reactive water.

By "non-hygroscopic" is meant a composition lacking a hygroscopic property, i.e., the tendency of the substance to hydrate by absorbing water, usually from the ambient humidity. The base material should be non-hygroscopic at ambient temperatures and humidities usually encountered during handling and storage. The composition of the invention may comprise materials that are hygroscopic, but they must be present in small enough amounts to retain the non-hygroscopic nature of the entire base composition. Essentially the substantial portion of the base material should be non-hygroscopic. The base is a solid, i.e., a solid or semisolid material such as a candy, gum, tablet, paste, or any solid or semisolid form capable of being placed in the mouth and which is dissolvable to release the carbamide peroxide to the surface of the tooth.

The substantial portion of the base composition is preferably isomalt. A derivative of sucrose, isomalt is an equimolar mixture of two isomeric disaccharide polyols, α-D-glucopyranosyl-1,6-D-sorbitol (GPS) and α-D-glucopyranosyl-1,1-D-mannitol (GPM). Isomalt is sold under the trademark Palatinit™ by Palatinit Süssungsmittel GmbH, Mannheim, Germany. Isomalt is non-hygroscopic, particularly at ambient temperatures and humidities. At 25° C. isomalt absorbs very little water. At temperatures as high as 60° C. and 80° C. the relative humidity must be 75% and 65% respectively for significant water absorption. A detailed discussion of isomalt and its various properties is disclosed in *Isomalt*, by Peter Sträter and William E. Irwin in Alternative Sweeteners, edited by Lyn O'Brien Nabors and Robert C. Gellardi, Marcel Dekker, Inc., 1992.

Other suitable base materials include other non-hygroscopic materials, and may include, but not be limited to disacharide materials, and sweetening compounds with a low molecular polarity.

The base composition may comprise other suitable ingredients that are used in orally administered compositions, such as flavors, sweeteners, anti-oxidants, stabilizers, colorants, and the like.

The composition of the invention is made by incorporating the carbamide peroxide whitening compound into the solid base material by first heating the base material to a temperature sufficient to drive off any water in the composition. For isomalt, this is a temperature of about 150° C. or above. The base material is then cooled to a temperature at which the carbamide peroxide can be incorporated and mixed into the base material. As the temperature approaches near 120° C., the carbamide peroxide disassociates. Accordingly, the preferred mixing temperature is 118° C. or below. When isomalt cools to near 110° C. it becomes difficult to mix the carbamide peroxide in an isomalt base. Accordingly the preferred temperature for mixing in isomalt is 114° C. or above. In summary, for mixing carbamide peroxide in isomalt, the mixing temperature is preferably between 114° C. and 118° C., more preferably about 116° C.

After incorporating the carbamide peroxide, the material is then allowed to solidify. The solid base can be formed into hard candy shapes by any suitable method, or crushed into powder and then hard pressed in to tablets, or otherwise processed by conventional methods into a solid form that can be orally administered. Basically, any process that permits the heating to expel the water and the mixing temperature of the carbamide peroxide is suitable for the present invention. The other components of the composition, i.e., the sweeteners, stabilizers, flavors, etc. are added at any suitable time, as dictated by their properties.

When the composition of the invention is placed within the mouth, the composition slowly dissolves adjacent to the teeth which provides an effective amount of the carbamide peroxide to the surface of the tooth. Preferably, a candy or tablet of the invention is composed to dissolve slowly over about a 20 minute period. A consistent daily use of the tablets of the invention will then obtain a maximum whitening of the teeth of the consumer.

BRIEF DESCRIPTION OF THE DRAWINGS

The sole FIGURE is a flow diagram of a process of the invention.

DETAILED DESCRIPTION OF THE INVENTION

Referring to the FIGURE which is a flow sheet of the method of the invention, a non-hygroscopic base is provided and heated to 150° C. to drive of the water in the base. The base is cooled to 116° C., the temperature at which carbamide peroxide is added and mixed. The material is then allowed to cool to form a solid material.

EXAMPLES

Example I
Hard Candy Composition

Candy bases were made and formed into hard candies according to the invention.

A base mixture comprising isomalt and the ingredients shown in Table A were compounded by conventional candy making technique and then heated to a temperature of 150° C. for a sufficient period to drive of any free water. The mixture was then cooled to 116° C. and the active ingredient, carbamide peroxide, was added. The other ingredients were added and compounded according to standard candy making practice. The composition was then allowed to cool and was molded formed into candy shapes by conventional techniques. Alternately, the composition is allowed to solidify, ground, and the ground composition pressed into tablets. The amounts of the ingredients in percent, based upon the original unheated mixture and the final product are shown in Table A.

TABLE A

CANDY FORMULATION

|  | Mixture (wt. %) | Final Composition (wt. %) |
|---|---|---|
| Base Ingredients |  |  |
| Isomalt | 78.0 | 93.19 |
| Titanium Dioxide | 0.2 | 0.24 |
| Aspartame | 0.85 | 1.0 |
| Deionized Water | 16.30 | — |
| Flavoring (Pina Cola) | 0.65 | 0.78 |
| Active Ingredient |  |  |
| Carbamide Peroxide | 4.0 | 4.78 |

Example II

A candy composition was made, essentially as in Example I, except a different flavor was used. The amounts of the ingredients as a percentage of the initial mix are shown in Table B.

TABLE B

CANDY FORMULATION

|  | Mix (wt. %) |
|---|---|
| Base Ingredient |  |
| Isomalt | 78.0 |
| Titanium Dioxide | 0.2 |
| Aspartame | 0.85 |
| Flavoring (Spearmint) | 0.40 |
| Water | 16.55 |
| Active Ingredient |  |
| Carbamide Peroxide | 4.0 |

Example III

A hard candy composition was made essentially as in Example I except that Vitamin E was added as an antioxidant and a preservative. The amounts of the ingredients as a percentage of the initial mix and the composition of the final product are shown in Table C.

TABLE C

VITAMIN E CANDY FORMULATION

|  | Mix (wt. %) | Final Composition (wt. %) |
|---|---|---|
| Base Ingredient |  |  |
| Isomalt | 78.2 | 90.20 |
| Titanium Dioxide | 0.2 | 0.23 |
| Aspartame | 0.85 | 0.98 |
| Water | 13.30 | — |
| Flavoring (Cherry) | 0.65 | 0.75 |
| Vitamin E | 3.0 | 3.46 |
| Active Ingredient |  |  |
| Carbamide Peroxide | 3.8 | 4.38 |

Example IV

A composition was produced in the form of a tablet. This accomplished by mixing essentially water-free isomalt in a powder form with the other ingredients also in powder form, and pressing the powder mixture into tablets by conventional techniques. Isomalt is available commercially in an essentially water-free condition. Alternately, the isomalt may be heated to 150° C., resolidified and ground to form a power. The base composition was mixed, heated to 150° C. for sufficient time to drive off the free water. The composition of a tablet in grams and wt. % of the ingredients are shown in Table D.

TABLE D

TABLET COMPOSITION 10% ACTIVE INGREDIENT

|  | Grams | (wt. %) |
|---|---|---|
| Base Ingredient |  |  |
| Isomalt | 50 | 79.66 |
| Citric Acid | 0.2 | 0.32 |
| Vanilla | 3.5 | 5.58 |
| NutraSweet | 0.95 | 1.51 |
| Magnesium Stearate | 1.5 | 2.39 |
| Peppermint Oil | 0.32 | 0.51 |
| Active Ingredient |  |  |
| Carbamide Peroxide | 6.3 | 10.04 |
| TOTAL | 62.77 | 100.00 |

Example V

This example illustrates a paste composition of the invention. A composition of the invention in a semisolid paste form is manufactured by blending, using conventional toothpaste technology ingredients, in the amounts listed in Table E. The result is a tooth-paste composition that may be used for whitening teeth. Other ingredients used in conventional tooth-paste manufacture may also be used, as long as the composition is compounded without the addition of the water that would react with the active ingredient.

TABLE E

TOOTHPASTE COMPOSITION

|  | Grams |
| --- | --- |
| Base Ingredient | |
| Dicalcium Phosphate Dihydrate | 27.7 |
| Glycerin | 17.8 |
| Sorbitol | 16.7 |
| Hydrated Silica | 2.2 |
| Flavor (Peppermint/Wintergreen) | 1.1 |
| Cellulose Gum | 2.8 |
| Isomalt | 11.1 |
| Sodium Bicarbonate | 11.1 |
| Sodium Saccharin | 1.1 |
| Sodium Laurel Sulfate | 2.8 |
| Active Ingredient | |
| Carbamide Peroxide | 5.6 |
| TOTAL | 100.0 |

Comparative Examples

Compositions were made, essentially as described in Example I, except that hygroscopic base materials were substituted for the isomalt. The final product was stored in ambient room-temperature/humidity conditions and periodically tested for taste and amount of active ingredient (AI) remaining in the composition.

The hygroscopic base materials used were mannitol, sorbitol, and xylitol. In compositions with these materials there was a noticeable urea taste after 2 days. The amount of the carbamide peroxide active ingredient decreased from 4 wt. % to 2 wt. % in 6 days. Basically, for all the comparative compositions made from hygroscopic bases, the composition became uneﬃcacious and unpalatable in less than one week due to the decomposition of the carbamide peroxide.

As a comparison, composition made according to Examples I to IV above were made and stored under similar conditions. After one month there was no detectable change in taste and no detectable decrease in the amount of carbamide peroxide.

As seen from the above data, the use of a non-hygroscopic base material is critical to the invention. The candy compositions with the comparative base materials all exhibited poor shelf life. This was due to the hygroscopic nature of the base material that rendered the carbamide peroxide unstable. In comparison, the composition of the invention shows excellent shelf life with no urea taste nor significant deterioration of the carbamide peroxide.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A tooth-paste composition for a tooth whitening composition comprising;
   carbamide peroxide in an amount effective to dissolve and produce a whitening effect on teeth when the composition is used in the mouth,
   a solid, water-free, non-hygroscopic base comprising isomalt, with water in the composition at sufficiently low amount and the composition being sufficiently non-hygroscopic to provide a stable composition with respect to the decomposition of carbamide peroxide in the presence of water.

2. The composition of claim 1 wherein the carbamide peroxide is present in an amount between 3.5 weight percent and 10 weight percent, based upon the total weight of the composition.

3. The composition of claim 1 wherein the carbamide peroxide is present in an amount between 3 weight percent and 12 weight percent, based upon the total weight of the composition.

4. A method for manufacturing a tooth-paste whitening composition comprising
   compounding an essentially water-free, non-hygroscopic tooth-paste base and a tooth-whitening amount of carbamide peroxide,
   the water-free, non-hygroscopic base comprising isomalt, with water in composition at sufficiently low amount and the composition being sufficiently non-hygroscopic to provide a stable composition with respect to the decomposition of carbamide peroxide in the presence of water.

5. A method of whitening teeth comprising;
   placing in the mouth a solid composition comprising carbamide peroxide in an amount effective to produce a whitening effect on teeth when the composition is used in the mouth, and a solid, essentially water-free, non-hygroscopic base,
   the solid, water-free, non-hygroscopic base comprising isomalt, with water in the composition at sufficiently low amount and the composition sufficiently non-hygroscopic to provide a stable composition with respect to the decomposition of carbamide peroxide in the presence of water.

* * * * *